US008642337B2

(12) United States Patent
Kiessling et al.

(10) Patent No.: US 8,642,337 B2
(45) Date of Patent: *Feb. 4, 2014

(54) DEFINED SURFACES OF SELF-ASSEMBLED MONOLAYERS AND STEM CELLS

(75) Inventors: Laura L. Kiessling, Madison, WI (US); Ratmir Derda, Madison, WI (US); Brendan P. Orner, Singapore (SG); James A. Thomson, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/291,555

(22) Filed: Nov. 8, 2011

(65) Prior Publication Data

US 2012/0135518 A1    May 31, 2012

Related U.S. Application Data

(63) Continuation of application No. 11/504,573, filed on Aug. 15, 2006, now Pat. No. 8,062,890.

(60) Provisional application No. 60/708,167, filed on Aug. 15, 2005.

(51) Int. Cl.
| C12N 5/00 | (2006.01) |
| C12N 5/02 | (2006.01) |
| C12N 5/071 | (2010.01) |
| C12N 1/00 | (2006.01) |

(52) U.S. Cl.
USPC ........... 435/395; 435/402; 435/366; 435/375; 435/283.1

(58) Field of Classification Search
None
See application file for complete search history.

(56) References Cited

U.S. PATENT DOCUMENTS

| 2007/0026518 A1 | 2/2007 | Healy |
| 2007/0128175 A1 | 6/2007 | Ozbas |
| 2007/0207543 A1 | 9/2007 | Kiessling |
| 2010/0068793 A1 | 3/2010 | Ungrin |
| 2010/0189760 A1 | 7/2010 | Schaffer |

FOREIGN PATENT DOCUMENTS

WO    WO2004055155    7/2004

OTHER PUBLICATIONS

Mrkisch, M et al , 1997, Experimental Cell Research, 234:305-313.*
Pikkarainen, T et al, Journal of Biological Chemistry, 1988, 14:6751-6758.*
Orner, 2004,J Am Chem Soc, 126:10808- 10809.*
Xu et al, 2001, Nature Biotechnology, 19:971-974.*
Derda et al., Defined substrates for human embryonic stem cell growth identified from surface arrays. ACS Chem. Biol. May 22, 2007;2(5):347-55.
Klim et al., A defined glycosaminoglycan-binding substratum for human pluripotent stem cells. Nature methods 2010;7(12):989-94.
Brovelli, D. et al.,"Highly Oriented, Self-Assembled Alkanephosphate Monolayers on Tantalum(V) Oxide Surfaces," Langmuir, vol. 15, No. 13,pp. 4324-4327, 1999.
Laibinis, P. E. et al.,"Comparison of the structures and wetting properties of self-assembled monolayers of n-alkanethiols on the coinage metal surfaces, copper, silver, and gold," J. Am. Chem. Soc., vol. 113,No. 19, 7152-7167 , 1991.
Li, Z.et al., "Self-Assembly of Alkanethiol Molecules onto Platinum and Platinum Oxide Surfaces," Langmuir, vol. 19, No. 17,pp. 6744-6749, 2003.
Love, J. C. et al., "Formation and Structure of Self-Assembled Monolayers of Alkanethiolates on Palladium,". J. Am. Chem. Soc. ,vol. 125, No. 9, pp. 2597-2609, 2003.
Muskal, N. et al, "Self-assembled monolayers on mercury surfaces,". J. Electroanal. Chem., vol. 409, No. 1-2, pp. 131-136, 1996.
Ullman, A.; "Formation and Structure of Self-Assembled Monolayers," Chem. Rev., vol. 96, No. 4, pp. 1533-1554, 1996.
Walczak, M. et al.,"Structure and interfacial properties of spontaneously adsorbed n-alkanethiolate monolayers on evaporated silver surfaces," J. Am. Chem. Soc., 113, No. 7, 2370-2378,1991.
Khademhosseini, et al., "Co-culture of human embryonic stem cells with murine embryonic fibroblasts on microwell-patterned substrates," Biomaterials 27, 5968-5977 (2006).
Anderson, et al., "Nanoliter-scale synthesis of arrayed biomaterials and application to human embryonic stem cells," Nature Biotechnology, vol. 22, No. 7, 863-866 (2004).
Falsey, et al., "Peptide and Small Molecule Microarray for High Throughput Cell Adhesion and Functional Assays," Bioconj. Chem 2001, 12, 346-353.
Hartgerink, et al., "Self-Assembly and Mineralization of Peptide-amphiphile nanofibers," Science vol. 294, 1684-1688 (2001).
Hoffman & Carpenter, "Characterizaation and culture of human embryonic stem cells," Nature 23:6; 699-708 (2005).
Imreh, et al., "Culture and Expansion of the Human Embryonic Stem Cell Line HS181, Evaluated in a Double Color System," Stem Cells & Dev. 13:337-343 (2004).
Orner, et al., "Array for the Combinatorial Exploration of Cell Adhesion," J. Am. Chem. Soc. 2004, 126, 10808-10809.
Thompson, et al., "Embryonic Stem Cell Lines Derived from Human Blastocysts," Science 282, 1145-1147 (1998).
Xu, et al., "Feeder-free Growth of undifferentiated human embryonic stem cells," Nature, 19:971-974 (2001).
Amit, M, et al., "Feeder layer- and serum-free culture of human embryonic stem cells," Biol. Reprod. 70:837-845 (2004).
Emami Shahriar H et al, Self-renewal and proliferation of murine embryonic stem cells: A study of glycoaminoglycans effect on feeder-free cultures, Journal of Bioactive and Compatible Polymers. vol. 22 No. 3 pp. 314-322 (2007).
Fromm, J.R., et al., Pattern and Spacing of Basic Amino Acids in the Heparin Binding Sites, Arch. Biochem. Biophys. 343:92 (1997).

(Continued)

Primary Examiner — Valarie Bertoglio
(74) Attorney, Agent, or Firm — Quarles & Brady LLP

(57) ABSTRACT

A method for the construction of arrays from self-assembling monolayers is described. The arrays have particular utility for the screening of peptides ligands that can foster the growth of cells in culture. This technique has been used to identify peptide ligands that foster the growth of human stem cells, which otherwise require an extracellular matrix in order to grow in an undifferentiated state. This also makes possible an assay to identify other such peptides.

6 Claims, 9 Drawing Sheets

(56) References Cited

OTHER PUBLICATIONS

Jackson RL et al. "Glycosaminoglycans molecular properties protein interaction and role in physiological processes" Physiological Reviews, American Physiological Society, US. vol. 71 No. 2 pp. 481-540 (1991).

Braam, S., et al., "Recombinant vitronectin is a functionally defined substrate that supports human embryonic stem cell self renewal via αVβ5 integrin," Stem Cells [Epub ahead of print, Jul. 17, 2008].

Ludwig, T. et al., "Derivation of human embryonic stem cells in defined conditions," Nat. Biotechnol. 24:185-187 (2006).

Wantanabe et al. "A ROCK inhibitor permits survival of dissociated human embryonic stem cells". Jun. 1, 2007, pp. 681-686, vol. 25, No. 6, Nature Biotechnology.

Pikkaraien,T et al., Journal of Biological Chemistry, 1998, 14:6751-6758.

Mrkisch, M. et al., 1997, Experimental Cell research, 234:305-313.

Anderson et al., Nanoliter-scale synthesis of arrayed biomaterials and application to human embryonic stem cells, Nat. Biotechnol. 22:863 (2004).

* cited by examiner

DEFINED SURFACES OF SELF-ASSEMBLED MONOLAYERS AND STEM CELLS

CROSS-REFERENCE TO RELATED APPLICATIONS

This application is a continuation of U.S. Utility patent application Ser. No. 11/504,573, filed Aug. 15, 2006, now U.S. Pat. No. 8,062,890, which claims the benefit of U.S. Provisional Patent Application No. 60/708,167, filed Aug. 15, 2005, each of which is incorporated herein by reference as if set forth in its entirety.

STATEMENT REGARDING FEDERALLY SPONSORED RESEARCH OR DEVELOPMENT

This invention was made with government support under N66001-03-1-8932 awarded by the NAVY/ONR and 0079983 awarded by the National Science Foundation. The government has certain rights in the invention.

BACKGROUND

Stem cells are defined as cells that are capable of a differentiation into many other differentiated cell types. Embryonic stem cells are stem cells from embryos that are capable of differentiation into most, if not all, of the differentiated cell types of a mature body. Stem cells are referred to as pluripotent, which describes this capability of differentiating into many cell types. A category of pluripotent stem cell of high interest to the research community is the human embryonic stem cell, abbreviated herein as hES cell, which is an embryonic stem cell derived from a human embryonic source. hES cells are of great scientific interest because they are capable of indefinite proliferation in culture and are thus capable, at least in principle, of supplying cells and tissues for replacement of failing or defective human tissue. Methods to culture human embryonic stem cells offer the potential of unlimited amounts of human cells and tissues for use in a variety of therapeutic protocols to assist in human health. It is envisioned that in the future hES cells will be proliferated and directed to differentiate into specific lineages so as to develop differentiated cells or tissues that can be transplanted into human bodies for therapeutic purposes.

One of most significant features of hES cells is the attribute of being capable of self-renewal. By that it is meant that the hES cells are capable of proliferating into multiple progeny stem cells, each of which seems to have the full potential of its ancestor cell. In other words, the progeny are renewed to have all the developmental and proliferative capacity of the parental cell. This attribute, combined with the pluripotency, are the traits that make hES cells candidates for many potential uses, since, in theory, hES cells can be reproduced indefinitely and in large numbers and then induced to become any cell type in the human body. The attribute of ability to self-renew appears closely linked to the attribute of being undifferentiated in the sense that at least given present knowledge, only undifferentiated hES cells are capable of indefinite self-renewal and as soon as the cells differentiate, the attribute of self-renewal capability is lost. Since hES cells will spontaneously differentiate, care must be taken in culture conditions to maintain the cells in an undifferentiated state.

Among the factors that have so far been identified as successful in maintaining hES cells in long term culture in an undifferentiated state are the medium in which the cells are grown and the substrate on which they are grown. Much progress has been made in defining media, which can be formulated to include the activators of FGF and TGF-beta pathway and suppressors of BMP and WNT pathways, which have the effect of enhancing the cells self-renewal. Considerably less information is available on the role of substrates and cell-substrate adhesion in hES cell survival and growth.

In the original co-culture experiments, hES cells were plated on a gelatin-coated surface containing mouse embryonic fibroblasts (MEFs) or other feeder cells. Thomson et al., *Science* 282, 1145-1147 (1998). Upon plating, it was found that the hES cells do not grow on top of feeder cells, but instead tend to occupy the exposed gelatin-coated surface. As the hES cells proliferate, these feeder cells are "pushed away" by the growing ES cell colony. Imreh et al., *Stem Cells and Development,* 13, 337-343 (2004). This observation suggests that the gelatin-coated surface along with the secreted factors provide a sufficient platform for the attachment. It was also discovered that growth of cells on feeder layers can be avoided through the use of "conditioned medium" or CM, which is medium in which feeder cells have been cultured. However, culture of hES cells on simple gelatin-coated surfaces even in CM leads to rapid differentiation of the cells. Xu et al., *Nat. Biotechnol.* 19, 971-974 (2001). To date, growth of undifferentiated ES cells without exposure to feeder cells has been achieved on surfaces coated with lysed MEFs in a medium containing FGF and LIF, laminin in MEF-CM, fibronectin in the media containing LIF, bFGF and TGF-beta and Matrigel®-coated surface in various media conditions. (e.g., Xu, supra; Amit et al., *Biol. Reprod.* 70, 837-845 (2004); Hoffman & Carpenter, *Nat. Biotechnol.* 23, 699-708 (2005)). Matrigel® is a commercially produced extracellular matrix material. Interestingly, there have been other reports mentioning the failure of ES cell culture in the presence of MEF-CM on surfaces coated with fibronectin, laminin and Matrigel®. A recent review summarizing advances in hES cell culture techniques attributes this variability to multiple factors including variability in media formulations, variability in feeder types used for CM production, batch-to-batch variability of the attachment substrates or even variability between hES cell lines including origin, passage number, karyotypic stability and epigenetic status. (Hoffman, supra).

It is important not to neglect the role of substrate attachment for successful hES cell growth. Identifying defined hES cell growth conditions requires the identification of defined growth media and a defined hES cell attachment surface. Screening well-defined surfaces in an array format allows rapid identification of specific molecules that promote hES cell adhesion. Because of the relatively small amount of the materials (e.g., cells and media) required to screen for cell adhesion to a surface microarray, the screen can be easily repeated and performed in parallel for multiple ES cell types and media formulations. Thus, this strategy offers a low-cost and rapid means to find defined conditions and therefore tame the variability present in hES cell culture literature.

To date, several successful examples of multicomponent microarrays in cell-based screens have been reported. Lam and co-workers fabricated a peptide-array prepared by contact spotting of peptides onto glyoxylyl-functionalized glass slides. Falsey et al., *Bioconjug. Chem.* 12, 346-353 (2001). These arrays were used to identify peptides promoting adhesion of a specific cancer cell line. Bhatia and co-workers presented fabrication of a microarray presenting combinations of several proteins fabricated via contact printing onto acrylamide-coated glass slides. This array was used to screen for protein combinations that assist the differentiation of mouse ES cell into hepatocytes. Langer and coworkers fabricated an array of polymeric materials by spotting combinations of monomers onto a glass slide followed by in situ polymerization. Subsequently, they used a collection of cells obtained by trypsinization of embryonic bodies derived from hES cells and identified several polymers promoting cell adhesion and differentiation in the presence of retinoic acid. A similar approach was recently reported to screen for materials promoting adhesion of the mesenchymal stem cells. However, no reports to date have described screening for growth of undifferentiated hES cells. Identifying such conditions is challenging: The undifferentiated state of hES cells is easily disrupted by small changes in their growth environment, an attribute that has hindered the development of a reliable and reproducible assay to assess a variety of growth conditions.

BRIEF SUMMARY

The present invention involves three interrelated concepts. The first concept is the use of alkane thiols (ATs) to construct self-assembled monolayers (SAMs) in an array. The second concept is to use peptide ligands attached to the ATs in selected areas of the array to test for ligands to which human embryonic stem cells will adhere. The third concept is to identify peptide ligands that will support the culturing of human embryonic stem cells on such arrays.

The present invention is thus summarized in one aspect as a monolayer array that is a SAM of AT molecules to which is attached selectively moieties intended either to encourage or discourage the contact of solutions and the adherence of cells to particular defined locations in the array.

The present invention is also summarized in a second aspect as a method to identify and define which peptides can be used to support the culture of hES cells by making an array from a SAM in which defined areas of the array present different peptides to cells placed on the array surface in order to determine which peptides support the growth of hES cells in culture.

The present invention is also summarized in a third aspect as defined peptides to which hES cells will adhere in a SAM array so as to culture and localize the hES cell colonies.

Other objects, features and advantages of the present invention will become apparent from the following specification.

DETAILED DESCRIPTION OF PREFERRED EMBODIMENTS

Figure 1:
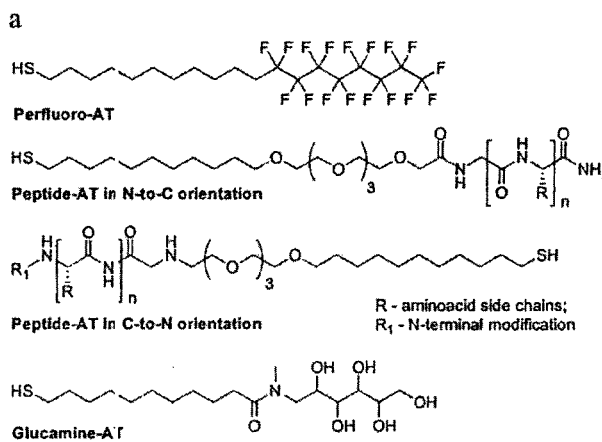
FIG. 1 illustrates the structure of ATs species used in a cell adhesion screen for hES cells, and the results of hES cell growth on various peptides in the array.
Figure 1:
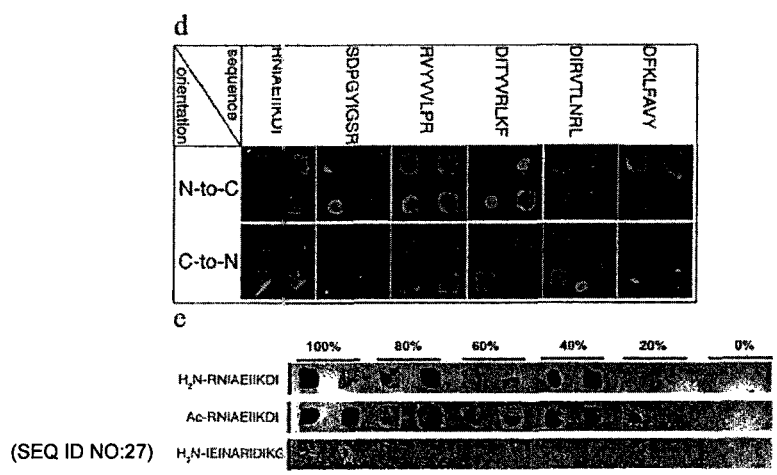

What is described here first is a method to use SAM chemistry to construct arrays that can be used to present ligands to cells plated onto the array. The arrays are preferably constructed of SAMs such as those formed using ATs. An advantage of using ATs is that they form reproducible SAMs and surfaces. This attribute means that the array elements will vary only because of the peptide or other binding element presented on the array and not because of other bulk properties of the array, such as topology. This method of array formation can be used to identify specific ligands or epitopes that act to promote hES cell binding or self-renewal. To construct such an array, we desired to utilize a method to pattern the SAM array so that ligands would only be presented to the cells in defined areas of the arrays and that other areas of the array (the background areas) would resist both solvents and cell presence.

The SAMs permit distinct formulations for the background areas of the array and the elements of the array. The background areas between the array elements have a property referred to as "solvophobic," or resistant to the spreading of solvents. The background should also be cytophobic to resist cellular attachment. In the array elements, we desired to be able to spot areas that would present specific ligands or epitopes on their surface. The ligands would often be peptides, but can also be small organic molecules.

To satisfy these criteria, a strategy of forming a SAM was adopted using AT chemistry on gold in all the areas of the array. For, example, a background was formed of perfluoro-AT that was both cytophobic and solvophobic. First, the surface was coated with a perfluoro-AT monolayer, either leaving holes in the monolayer for the elements of the array or creating holes in the monolayer for the elements of the array in a subsequent step. In the elements of the array, AT species carrying various ligands could then be attached to the substrate in the holes to complete the monolayer and to present ligands for cellular attachment in each element. The strategy here is to coat a gold surface with perfluoro-AT, leaving or creating "holes" in the array into which AT species with specific ligands, also referred to here as epitopes, attached are then spotted. Methods for synthesizing the AT species for both regions on the array are found in more detail in the examples below.

Each AT species may be thought of as having three important regions or moieties. One region is at the basal end, which is an attachment moiety intended to attach the monolayer species to the substrate. In the case of the AT species, the attachment moiety is the thiol groups, which attaches to a gold substrate. Other attachment groups can attach to other substrates. Another region is the intermediate region, which is the spacer moiety, and in this case the alkane. Other simple organic groups can be used for the spacer as long as the resulting species are capable of self-assembly in a monolayer. Lastly, the active group at the end of the monolayer species is the ligand, which can be a group intended to repel cells (cytophobic) or to bind cells (cytophilic). The ligands intended to bind cells, or to test binding to cells, can be, but are not limited to peptides.

This system offers the ability to determine the peptide ligands that will foster cell growth for cell types that require extracellular signals for desired growth properties. In particular, this system can be used to test peptide ligands to identify those which help to foster self-renewal and, thus, the undifferentiated growth of hES cells. Arrays can be fabricated that contain differing peptide elements in AT-peptide species spotted in different array elements. After depositing hES cells on the array, the elements that support the growth of hES cell colonies will preferentially present those peptides to which ES cells preferentially bind and grow. This same strategy can be used to identify and find differentiated progeny lineages from mixed populations of ES cells and differentiated progeny cells of similar or varied type.

Thus, in this specification, we also describe how we have used a SAM array format to identify surfaces that promote the self-renewal of hES cells. These cells typically grow in colonies of various size randomly distributed on growth substrate. Unlike most conventional cells that are grown in culture, ES cells undergo rapid differentiation and/or death if they are cultured as a confluent monolayer. Therefore, one of the key factors in the ES cell culture is control over ES cell density. However, when any cells are cultured in an array format they proliferate independently in each array element and "density of the culture" is different for each array element. Therefore, the duration of the experiment in array format must be carefully balanced to avoid false-negative outcomes that can arise when array elements present cells at high-density. Subtle variations in cell density cannot be eliminated in multi-component arrays, because each array element presents a slightly different environment for cell proliferation. Still, this parameter can be minimized if the initial cell distribution is uniform throughout the array elements. Control over cell density can be readily achieved with a majority of conventional cell lines; however, it is not trivial to do so with hES cells.

Conventional array fabrication methods that utilize contact printing of small molecules onto functionalized surfaces yield random covalent or non-covalent immobilization of molecules onto the surface. This methodology will not afford reliable results in ES cell-based screens, due to poor control over array element geometry, ligand distribution, concentration and orientation on the surface of the array. In contrast, we have found that SAMs of ATs on gold, as discussed above, provide a well-defined system allowing state-of-the-art control over presentation of surface-immobilized molecules. We describe here an approach to the fabrication of the arrays of SAMs, and we demonstrate its utility for screening for cell adhesion and for the culture of human ES cells. We also show this technology to be compatible with ES cell growth conditions. Here we have also sought to extend this approach further and have demonstrated that a SAM-based microarray presenting a library of molecules can be used as a platform for discovery of novel, well-defined surfaces able to support proliferation of ES cells.

The starting point for design of the library of small molecules promoting ES-cell adhesion emerged upon careful examination of the components of the effective substrate Matrigel®. As mentioned, hES cells can be cultured on a Matrigel® substrate, but this isolated substrate contains extracellular matrix murine proteins in indeterminate quantities. Laminin, its major component, is known to interact with collagen and entactin (the other two major components) through globular domains and B2 short arm, respectively. Thus, these mixtures form a polymeric network with an organized display of particular protein subunits. The superiority of a Matrigel®-coated surface to a surface coated with pure laminin further suggests the necessity for the control over surface presentation of the binding domains of the proteins. Therefore, we sought to mimic both molecular and spatial composition of Matrigel® by assembling selected regions of the laminin on the surface with the highest degree of control over the presentation of the peptides. Extensive work has been done to map the biological activity of the laminin to specific chains, domains, and even short amino acid sequences. We have selected a variety of laminin-derived peptides known to exhibit strong biological activity (i.e. cell adhesion, neurite extension, angiogenesis, etc.) to construct the initial library.

The methods described herein have enormous potential that arises from interweaving synthetic chemistry and flexibility of SAMs to generate arrays for screening for ES cell adhesion. The exceptional degree of control over peptide ligand presentation and surface density provided by SAMs is useful for screening for any cell surface interactions and optimizing substrates for cells sensitive to their growth environment. Interactions of cells with their environment depend on surface concentration and presentation of the binding partners. Alteration of these parameters often influences the outcome of the cellular response. Embryo development presents the most fascinating example in which gradients of concentrations of the same effector molecules controls the differentiation pathways and morphological changes in the different spatial locations of the embryo. Simple knowledge of the structure of binding partners is not sufficient to explain these phenomena. We therefore contend that the next-generation of cell-based screening must involve technology allowing control over parameters beyond structure of the binding peptide. The SAM-based arrays presented here highlight the feasibility of such high-throughput multivariable screen on the single array surface.

Well-defined arrays of SAMs presenting small molecules present an important addition to currently reported techniques used for cell-based screening. Interaction of cells with SAMs presenting cell-binding peptides depends on the presence of a particular receptor in the cell and can be often attributed to a defined receptor-ligand pair. This reductionism in screening for cell-substrate interaction contrasts other approaches that involve a multitude of inseparable variables. For example, different cell types can bind to an array of extracellular matrix proteins utilizing a different set of receptors. This degeneracy in protein-cell interactions is hard to resolve using protein arrays, and it has to be addressed using other techniques. On the contrary, if they exist, specific cell surface receptor partners for bulk polymeric materials have yet to be identified; materials that incorporate particular recognition epitopes can be used to guide cells reproducibly to manifest specific states or behaviors. Although it is possible to screen for a polymeric material exhibiting a particular biological function, it is often impossible elucidate the mechanism for a particular material-specific biological activity.

The screen presented in this report utilized known fragments of laminin. Thus, the ability of some peptide sequences (e.g. RGD, YIGSR (SEQ ID NO:1), GNRWHSIYITRFG (SEQ ID NO:7)) to support ES cell growth can be explained using information about gene expression of their binding partners ($\alpha_v\beta_3$ and $\alpha_v\beta_5$ integrins, 37/64 kDa receptor, $\alpha_6\beta_1$ integrin) using reported ES cell gene expression profiles. For small molecules with no known binding partners, binding partners can be identified using established biochemical techniques. This technique enables the integration of receptor identification techniques with screening involving a large collection of small molecule ligands for specific cell-surface receptors. This will allow identification of the ES cell surface receptors involved in robust long-term growth and will suggest a mechanism by which signals induced by substrate adhesion control self-renewal of ES cells. Additionally, we have demonstrated that the findings of our screen can be extended to the design of materials supporting ES cell growth. Because the identified materials are fully synthetic they present no risk of contamination with animal products, and they can avoid problems of batch-to-batch variability of the materials of biological origin. Therefore, this technology provides an important contribution in the current quest for the state-of-the-art and well-defined ES cell growth conditions.

EXAMPLES

General Preparation of the Arrays of Self-Assembled Monolayers (Assembly After Conjugation Strategy): Chromium (1 nm) and then gold (25 nm) were evaporated onto piranha-cleaned glass coverslips (Corning No 1%, 23 mm squares) using a thermal evaporator (Denton Vacuum, Moorestown, N.J.). Substrates were immediately immersed into a 1 mM solution of fluoro-AT in absolute ethanol. After twenty-four hours, substrates were thoroughly rinsed with ethanol and dried under a stream of nitrogen. Coverslips with fluoro-AT SAM were irradiated with UV-light (1 kW, Hg—Xe Research Arc Lamp, Oriel Instruments (Spectra-Physics, Stratford, Conn.) through a quartz photomask (array of 500 μm or 750 μm squares, 0.067 quartz-chromium mask (Photo Sciences, Torrance, Calif.)) for 1 hour. Irradiated samples were rinsed thoroughly using several repetitive washes with absolute ethanol and distilled water and dried under a steam of nitrogen. Spotting of AT solutions onto the bare gold areas was performed within two hours of the photolithography. Spotting was performed manually using a P2-Pipetman (Gilson) in a humidity chamber. Spotted arrays were stored in the humidity chamber for twelve hours and thoroughly washed using repeated washes with ethanol and water. Rapid flow during washing was used to prevent cross-contamination of array spots.

Cell Culture: A neuroblastoma cell line, SH-SY5Y, was grown in 10% heat-inactivated fetal bovine serum (HI FBS), 45% high glucose Dulbecco's modified Eagle medium (DMEM), 45% Ham's F12 nutritional supplement (F12) with penicillin and streptomycin in an atmosphere of 5% $CO_2$ at 37° C. A fibroblast cell line, Swiss 3T3, was propagated in 10% HI FBS in DMEM. For plating of the cells on the chips, cells were incubated at 37° C. with 5% trypsin/ethylenediamine-tetraacetic acid (EDTA), centrifuged and resuspended in media at $2\times10^5$ cells/mL and $5\times10^5$ cells/mL for the fibroblasts and neuroblastomas, respectively. Chips were sterilized by placing each in a single well of a 6-well plate, soaking in 70% ethanol, and drying under UV light for 1 hour. To the individual chips was added 3 mL of the cell suspensions to each well. After 2-5 hours, the media was gently replaced three times and the chips were picked up, transferred to a clean well and 3 mL of media was added. The cells on the chips were typically propagated between 1-7 days. The media was then removed, and the cells were fixed in PFA buffer (2% paraformaldehyde, 350 mM NaCl, 150 mM HEPES, 10 mM $CaCl_2$, pH 7.4) for 20 minutes at 0° C. The cells were washed twice with Dulbecco's phosphate buffered saline and stained (0.1% Coomassie Brilliant Blue in $H_2O$/MeOH/AcOH (50:50:1)) for 5-15 minutes after which the cells were washed twice with water and air dried. Images were generated on a Leica MZ6 dissecting microscope.

Human Embryonic Stem Cell Propagation and Plating: The human ES cell line, H1, was grown on Matrigel®-coated plates in MEF-CM supplemented with 4 ng/mL basic fibroblast growth factor (bFGF). To produce CM, MEFs were seeded at a density of $2.12\times10^5$ cells/mL and fed medium consisting of DMEM/F12, 20% Knockout™ serum replacement, 2 mM L-glutamine, 1% minimal essential media non-essential amino acids and 0.1 mM β-mercaptoethanol. Both cell lines (H1 and MEF) were maintained at 37° C./5% $CO_2$ with CM collected, and cells fed approximately every 24 hours. Cell suspensions were made by treating with collagenase IV (1 mg/mL) for 10-12 minutes. The cells were scraped from the surface and suspended in CM.

Chips were sterilized as described above. To aid in ES cell patterning, the chips were then soaked in DMEM/F12 with 15% defined FBS for 1-2 hours and washed thoroughly. Then cells were plated on each chip ($1$-$2\times10^6$ cells/chip) and allowed to incubate overnight. The next morning the chips were moved to fresh wells and fed with CM.

Test for alkaline phosphatase activity: The procedure for staining for alkaline phosphatase activity was essentially identical to the procedure supplied by the manufacturer. After propagation of the ES cells, the media was removed. The reagents in 100 mM Tris pH 8.5 were incubated with the chips for 30 minutes at 25° C. The chips were washed gently for 5 min with Tris buffer and then fixed and dried as usual.

Initial experiments to test fluoro-AT SAM cytophobicity and cell patterning: Chips with a fluoro-AT SAM background and PEG acid-AT squares fabricated by immersion (vide supra) were plated with both SH-SY5Y neuroblastoma and Swiss-3T3 fibroblast cells that were either imaged as live cells or as fixed and stained cells. For both cell types, dense squares of cells on the cytophilic surface (PEG acid-AT) were formed. A minimal number of cells growing on the background were observed, thereby demonstrating the cytophobic property of the fluoro-AT SAM background.

Initial experiments to test cell response to SAM formation by spotting: A chip with a fluoro-AT SAM background surrounding bare gold squares was formed by photolithography. To this was spotted an aqueous solution (1 mM) of cytophilic PEG acid-AT in a pattern of 3×3 squares. An ethanolic solution of fluoro-AT was spotted on the remaining bare gold squares. Neuroblastoma SH-SY5Y cells were plated, proliferated, fixed and stained. A pattern corresponding to cells affixed to only the expected cytophilic surface was evident as was minimal binding to the cytophobic surface. This result demonstrates that spotting solutions of ATs can generate both cytophilic and cytophobic SAMs.

Solvophobicity Tests: Advancing contact angles were obtained for each of the surfaces with various solvents. Briefly, a small volume of solvent was added to the cleaned surfaces via syringe. As additional solvent was added the angle was measured through a magnifying bezel. Values from 180°-90° reflect a high degree of beading. As a benchmark, values for mixtures of water with polar-organic solvents were obtained for an undecanethiol SAM. (FIG. S2) A reduction in beading with increasing amount of organic solvent was observed. Polar organic solvents were chosen because these solvents dissolve most peptides and biologically active small molecule:. Measured values for 100% DMSO and 50% DMF are 61° and 72° respectively. The fluoro-AT SAM was the most effective at beading these solvents; this surface gives values of 80° and 92° for 100% DMF and 100% DMSO respectively.

To test the feasibility of spotting arrays with a hand held pipette, approximately 200 nL of water was spotted on the chips patterned with 750 μm hydrophilic PEG acid-AT squares surrounded by fluoro-AT SAM background. The water clearly formed beads due to the high contact angle between the solvent and the fluorinated surface. The importance of high contact angles of the background was reflected in that increased beading allows a high density of spots on a single chip. The higher the contact angle, more spots can be fit on the chip. A simple geometric rationale shows that the contact radium (ρ) of the liquid drop with volume (V) depended on the surface contact angle (θ) as:

$$\rho = \sin^{-1}\theta \, [(\pi/3V)(1-\cos\theta)(2+\cos\theta)]^{-1/3}$$

No gravity or surface tension effects are included in this analysis.

It was evident that the effective size (physical size) of a spot no longer changes for contact angles above 90°. The relevance of the solvophobicity of the fluoro-AT SAM background was that it provides contact angles above or near to 90° for a wider range of solvents than other hydrophobic surfaces and is also cytophobic.

Figure 4:
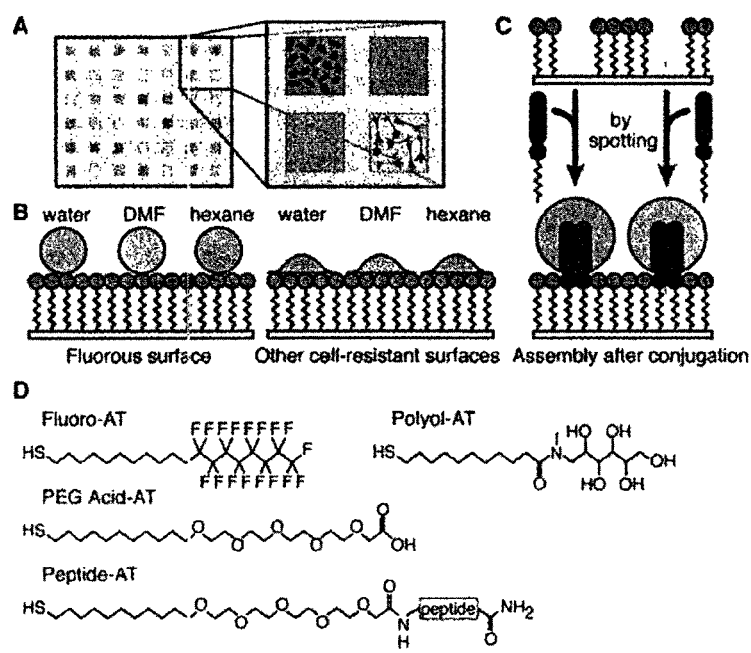
FIG. 4 is illustrates the arrangement of the array elements and the AT species used in the array.

To test the strategy for constructing arrays, we generated a patterned array with an AT known to bind to cells generally, PEG acid-AT, shown in FIG. 4, using cytophobic fluoro-AT as the background (also FIG. 4). Solutions of varying molar ratios of PEG acid-AT diluted with polyol-AT, a hydrophilic AT that does not interact with cells, were spotted on bare gold areas by photopatterning a SAM. Then, neuroblastoma (SH-SY5Y) cells and fibroblast (Swiss 3T3) cells were plated on the patterned surface, allowed to proliferate, fixed and stained. For both cell lines, measured cell adhesion decreased as the mole fraction of the acid in the spotting solutions approached 0.2. This indicates that the spotting method worked and that SAMs composed of mixtures of AT species can be screened as supports for cell cultures using this approach.

In physiological settings, cells interact with cues from the extra-cellular matrix in which they reside. The sequence Arg-Gly-Asp (RGD), found in a number of proteins, including fibronectin and vitronectin, binds a family of integrins on the surface of some cell lines, including the 3T3 fibroblasts. An Arg to Lys substitution in the motif destroys the adhesion. Alternatively, the peptide YIGSR (SEQ ID NO:1), a sequence found in the matrix protein laminin, interacts with the neuroblastoma cell line but not with the fibroblasts. To test whether surfaces that would preferentially react with defined cell lines could be created, a surface displaying a fluoro-AT SAM was photopatterned. Mixtures of polyol-AT and peptide-AT were then spotted on locations on the array in the areas of bare gold. As controls, an AT species known to bind cells generally, PEG acid-AT, was deposited in one element of the array and an AT species known to resist cell binding generally, polyol-AT, was deposited in another. Then neuroblastoma and fibroblast cells were deposited on the array, allowed to proliferate, fixed and stained. The fibroblasts bound to the RGD array element, bound minimally to the KGD element and bound modestly to the YIGSR element. The neuroblastoma cells adhered to the YIGSR element, but not to either of the RGD or KGD elements. Thus, cell-specific adhesion is possible with this system and specific to ligands for cell types.

To investigate the density issue, we ascertained how cell density, cell survival and even array element size can influence cell distribution in the array. A reverse time lapse analysis of ES cell aggregates (clumps) grown on Matrigel® in CM for 48 hours. An overlay of the colony outlines demonstrates that a typical colony originates from a very limited number of cell aggregates. A majority of the plated hES cells fail to attach and proliferate even on uniformly coated substrate. To find the array element size yielding reproducible ES plating conditions, we divided uniform substrate into areas of different size and estimated the survival rate as a function of a size. Visually, the substrate appears to be uniformly coated with cells one hour post plating. However, an analysis of cell survival demonstrates that only 50% of colonies deposited on the 0.2 mm square elements survived (or were viable) while 100% of the 0.8 mm elements contained viable colonies. The problem of survival cannot be solved by a simple increase in cell density due to problems associated with overgrowth-induced damage. Our analysis of projected area of cell growth additionally demonstrates the effect of cell aggregate size on survival rate. For cell clumps divided into large (>40 cells), medium (10-40 cells) and small (5-10 cells), survival rate in this particular example was 98%, 50% and 30%, respectively. This variability in cell aggregate size and cell survival rate inevitably lead to variability in the cell density in different array elements, even if the array elements presented the cells with the same growth substrate. For example, after 48 hours of proliferation cell, "density" ranges from 20% to 70% in different 0.8×0.8 mm elements.

This analysis underscores the importance of larger array element size in ES screens. These data highlight how the current trend in the technology towards miniaturization and fabrication of super high-density arrays may not be relevant for some cell surface arrays used for ES cells. With small array elements, ES cell survival will be stochastic, even on array elements presenting ligands that support hES cell self-renewal. When the size of the array elements is increased, those elements that can support hES cell self-renewal can be more reproducibly identified. Thus, screening results from arrays with elements that are too small will be inconclusive. More importantly, this analysis emphasizes the necessity for a high degree of control in array fabrication for ES cell based screens. When dealing with cell culture conditions for cells poised to undergo differentiation, it is important to ensure that variability is a consequence of cell growth rather than batch-to-batch reproducibility of the array.

We tested arrays of SAMs presenting a number of short peptides for their ability to support the growth of undifferentiated hES cells. The screen was done with the array presenting square elements of 0.5×0.5 mm (FIG. 1*b*) or 0.8×0.8 mm size (FIG. 1*c*). The 0.5×0.5 mm allowed 196 binding elements to be located on a single 22 mm square chip, and in turn the chip can easily fit in one well of a six-well culture plate. The ability of microarrays to localize multiple experiments to same a solution environment is invaluable for applications requiring frequent maintenance. For example, cultures of undifferentiated ES cell require daily changes of growth media. These changes can be easily performed on the entire microarray in one large well of a cell culture plate. For comparison, daily maintenance of experiments, on the same scale, performed in two 96-well plates, while practical, would require either significant human labor or specialized robotic equipment to function in a sterile environment to perform daily maintenance.

The images displayed in FIG. 1 illustrate the results from four independent experiments utilizing two different hES cell lines (H1 and H9; WiCell; Madison, Wis.) grown on defined surfaces. Cells grown on Matrigel® were detached using collagenase treatment and were plated on the microarray chip in the presence of CM. After twenty-four hours, media was replaced to remove dead and non-adherent cells. Attached cells were allowed to proliferate on the chip for five to six days and were supplement with fresh conditioned growth media daily. The experiment was stopped once cells reached 100% density in several (but not all) array elements. If continued, the cells in the array elements presenting 100% cell density usually detached, yielding square-shaped sheets of cells floating in solution, while cells in the other elements continued proliferation (not shown). This observation is consistent with those made earlier indicating cell growth variability in multi-component arrays and importance of the balanced duration of the experiment. Once the experiment was stopped, the cells were fixed and stained for markers of hES cell pluripotency. Specifically, we tested hES cell line H1 grown in 0.5×0.5 mm elements for the presence of endogenous alkaline phosphatase (FIG. 1*b*) and hES cell line H1 grown in 0.8×0.8 mm elements for the presence of Oct4 transcription factor (FIG. 1*c*). We have observed three general types of responses in these screens. Array elements presenting certain peptides promoted no or very little cell density at any plating conditions. These peptide regions most likely have no binding partners on ES cell surfaces. Alternatively, these peptides might be active for short term adhesion but incapable to initiate the adhesion-dependent signaling pathways controlling long-term ES cell proliferation. Several other peptide sequences were identified to yield reproducible square-shaped colonies, regardless of plating variability of the cells used for the experiment. These robust growth substrates present the greatest interest because they are relatively insensitive to variability in cell density, cell clump size, cell survival and other stochastic features outlined previously. These peptides are identified in the results presented in FIG. 1. Finally, the screen identified multiple peptide sequences exhibiting poorly reproducible ES cell adhesion, which varied not only from experiment to experiment but even within the same array. These observations indicate that for some peptides there is a degree of variability in ES cell survival and growth that can be different for different growth substrates. Of course, substrates exhibiting high variability in cell growth can hardly be useful for robust ES cell growth. On the other hand, identification of these ligands and their binding partners may be helpful in understanding the molecular basis for the tremendous heterogeneity in ES cell populations. Overall, these experiments demonstrated that multi-component arrays can be used for the identification of surfaces supporting ES cell adhesion and proliferation. We also show that screens in different growth conditions can be easily repeated with identical arrays providing valuable information about robustness of each adhesive surface.

As discussed above, the majority of other array fabrication techniques have no control over surface presentation of the surface-bound peptides, and in many cases, uncontrolled immobilization conditions in array fabrication can result in decreased activity of the immobilized ligands. In contrast, the orientatior of the peptides in these SAMs is highly uniform, and it is dictated solely by structure of the AT used for the fabrication of the SAM. Moreover, we have utilized facile solid-phase methodologies to synthesize peptides displaying AT-moiety on their N-terminus or C-terminus (FIG. 1a), selectively. Spotting of these ATs on gold yields SAMs displaying the same amino acid sequence in the opposite orientation (FIG. 1d). Thus, this method provides a means to identify a mode for presenting a binding peptide that provides optimal interactions with cells. Data from such experiments also can be used to suggest which part of the large peptide participates in the interaction with the receptor. An example of the latter is exemplified by the binding profile of the SDPGYIGSR (SEQ ID NO:2) sequence. This peptide contains a YIGSR recognition motif that binds 32/64 kDa laminin receptor expressed at a low level in ES cells. In our experiments, N-to-C orientation exposing YIGSR moiety supports cell adhesion for ES cells, albeit with moderate reproducibility. Switching the surface orientation hinders the YIGSR region and exposes the SDPG-portion and obliterates cell adhesion in the same plating environment. Thus, orientation as well as sequence is important to the cell adhesion and both can be selectively controlled using the SAM technique described here.

To test whether our screen can provide immediate information about the specificity of interactions, we explored the effect of sequence specificity, overall charge and surface density of a peptide binding site on its ability to support ES cell binding. The overall charge of the peptide was controlled by synthesizing the AT-peptides with either free or acetylated N-terminus. We assumed that the alteration of the charge on N-terminus in C-to-N orientation would have the most profound effect if the interaction of peptide with cell is non-specific. The surface density of the peptides in the SAMs can be easily controlled by co-assembly of peptide-AT with AT presenting no binding epitope (glucamine-AT, FIG. 1a). H1 cells were grown on the array presenting gradients of three peptides (FIG. 1e). We observed that the overall charge has no effect on cell binding to peptide, and both peptides exhibited cell binding in a similar range of surface concentrations. In contrast, the specific peptide sequence presented was critical: A peptide with a scrambled sequence exhibited negligible cell adhesion at 100% density, and no adhesions at any surface densities below 100%. These results indicate that the GRNIAEIIKDI (SEQ ID NO:3) peptide exhibits specific binding. Thus, the array of SAMs provides a simple means for assessing cell binding specificity, qualitative affinities and preferred binding orientation for each screened peptide on the single microchip. Most importantly, this requires no prior knowledge about the ligand binding mode or its partner receptor on the ES cell.

Figure 2:
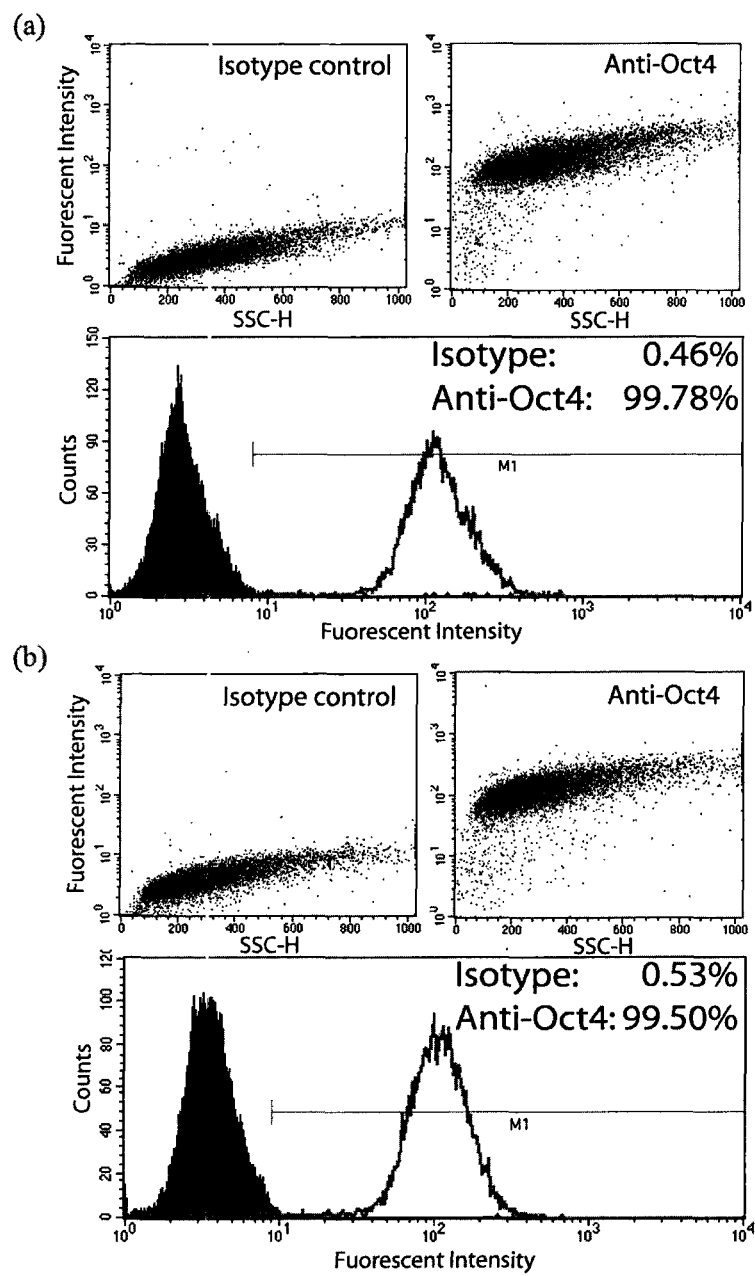
FIG. 2 illustrates the FACS analysis of hES cells proliferated on large areas of synthetic substrates.

Examination of the cell population within an array element provides a semi-quantitative indication of differentiation state of the ES cells. More rigorous analysis involves fluorescence-activated cell sorting (FACS) measurements to identify what population of the cells express specific markers of pluripotent stem cells. Therefore, we proliferated hES cells on gold-coated substrates of larger area (22×22 mm) containing one-component SAMs. FIG. 2a illustrate a representative FACS analysis of an ES cell population grown on a synthetic substrate after 1 week. Table 1 outlines the percentages of Oct4 positive cells obtained from each particular substrate. Not only can cells be grown on these substrates in the presence of MEF-CM, but some substrates retain their ability to support ES cell growth in defined growth media. Specifically, we tested hES cell line H9 grown in synthetic media supplemented with high concentrations of basic FGF (referred to as UM100, indicating presence of 100 mg/ml of FGF-2 among the other components). Importantly, these conditions support growth of undifferentiated hES cells on Matrigel®. FIG. 2b shows a FACS analysis of ES cells grown on SAMs presenting DITYVRLKF (SEQ ID NO:4) sequence in UM100 media. The indicated high level of Oct4 expression confirms their undifferentiated state after 1 week of culture.

TABLE 1

Summary of FACS analysis for ES cells proliferated on large areas presenting synthetic substrates.

| Sequence | Isotype (% population) | Oct4 (% population) |
|---|---|---|
| DITYVRLKF (SEQ ID NO: 4) | 0.46 | 99.78 |
| DIRVTLNRL (SEQ ID NO: 5) | 0.42 | 99.62 |
| GRYVVLPR (SEQ ID NO: 6) | 0.53 | 98.99 |
| GRNIAEIIKDI (SEQ ID NO: 3) | 0.50 | 98.12 |

These results demonstrate that SAMs present a rich and flexible foundation for the fabrication of microarrays. Moreover, SAMs can be fabricated on large enough areas to grow hES cells in any quantities. However, their fabrication requires gold-coated surfaces, which makes them inconvenient candidates for the ultimate growth substrate. Therefore, we sought to demonstrate that the results of our screen can also be readily utilized to fabricate a material more flexible in handling than SAMs on gold, yet exhibiting growth support for undifferentiated ES cells. This result would also suggest that screens utilizing a SAM-based array strategy for a particular cellular outcome (i.e. adhesion, growth, differentiation) can be immediately used as a starting point for the fabrication of advanced biomaterials exhibiting similar function.

Figure 3:
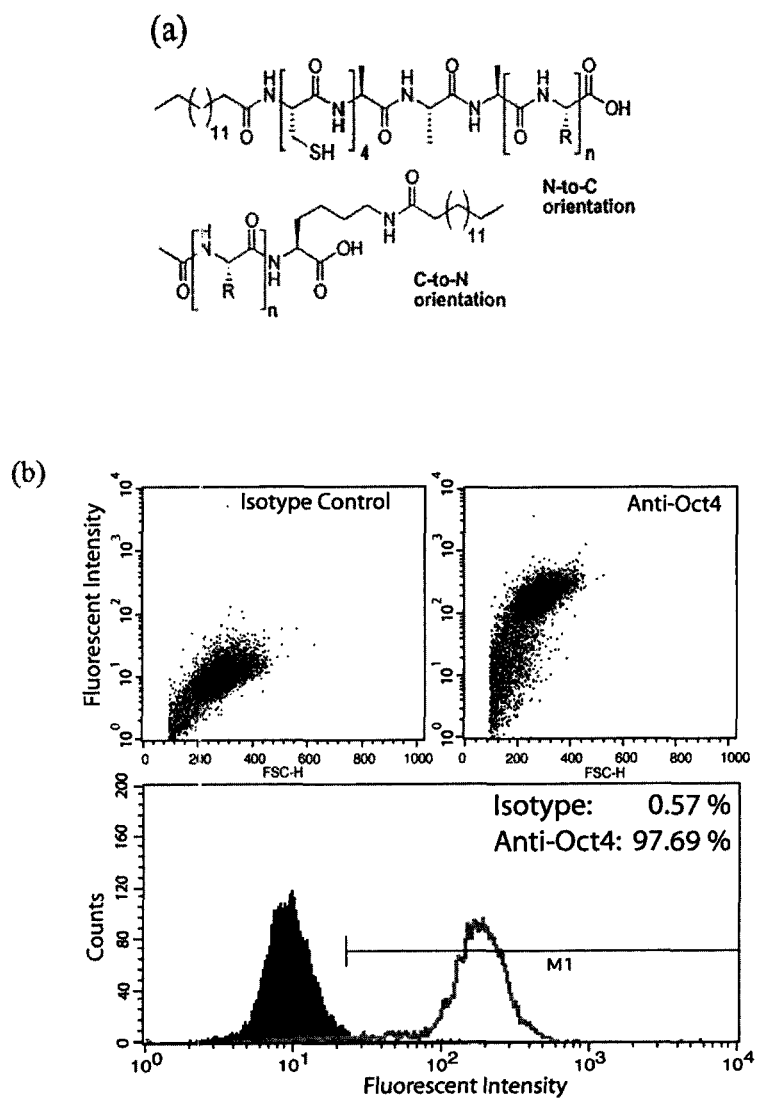
FIG. 3 illustrates the fabrication and utility of 3-dimensional substrates presenting identified ligand peptides for hES cell growth.

To allow a smooth transition from SAM-based screen to a material design, we aimed for the materials fabrication strategy yielding high control over peptide ligand presentation. Therefore, we utilized the approach pioneered by Stupp and co-workers (Hartgerink et al., *Proc. Natl. Acad. Sci. U.S.A.* 99, 5133-5138(2002)) to fabricate hydrogels composed of nanofibers presenting peptide ligands. Like SAMs, cylindrical nanofibers present peptide ligands or epitopes at a very high density and with a single, defined orientation. Additionally, we have envisioned that the control over the peptide orientation in the hydrogel can be readily achieved through simple solid-phase synthesis. Therefore all aspects of presentation of peptides in SAMs (FIGS. 1d-e) can be readily translated to those in hydrogels. To test this hypothesis, we synthesized amphiphiles presenting the GRNIAEIIKDI (SEQ ID NO:3) sequence in C-to-N and N-to-C orientation (FIG. 3a). Solutions of either of these peptides form a gel upon acidification. The formation of nanofiber morphology was confirmed by TEM. Indeed, this fabricated hydrogel can support adhesion and proliferation of ES cells, yielding undifferentiated ES population after one week as confirmed by FACS analysis for pluripotency marker Oct4 (FIG. 3b).

Differentiation Experiment: SIDQVEPYSSTAQ (FGF, SEQ ID NO:8) is known to bind FGF receptor. FGF signaling, in turn, can suppress hES cell differentiation. KIPKASSVP-TELSAISTLYL (SEQ ID NO:9) is known to bind BMP-receptor. BMP signaling induces hES cell differentiation. KKQRFRHRNRKG (VHB, SEQ ID NO:10) is a heparin binding motif from vitronectin. Vitronectin supports hES cell adhesion. RGD peptide is known to bind cell surface receptors (integrins) involved in adhesion of various cell types.

hES cells ($H_{1B}$) were passaged using the protease dispase from Matrigel® to the peptide surface arrays described above containing either BMP/RGD, BMP/VHB, FGF, FGF/RGD or FGF/VHB at various concentrations. hES cells were cultured on the arrays for thirteen days, fixed and stained by immunofluorescence. The cells were stained for a marker of pluripotency, Oct-4 (Green), and counterstained with DAPI (Blue). A combination of the FGF peptide mimic and the vitronectin heparin-binding motif supported hES cell self-renewal—the array element contained cells expressing Oct-4. Cells on the other array elements no longer express Oct-4 and are thus no longer pluripotent.

Synergy Experiment: hES cells ($H_{1B}$) were passaged using non-enzymatic methods from Matrigel® to the peptide surface arrays as described above (containing either RGD, FGF mimic or a combination of RGD and FGF mimic sequences). hES cells were cultured on the arrays for twenty-four hours and then fixed and stained by immunofluorescence. The cells were stained for a marker of pluripotency, Oct-4 (Red), and counterstained with DAPI (Blue). As opposed to when the peptides are arrayed individually, a combination of the two peptides promoted stronger short-term adhesion.

Figure 7:
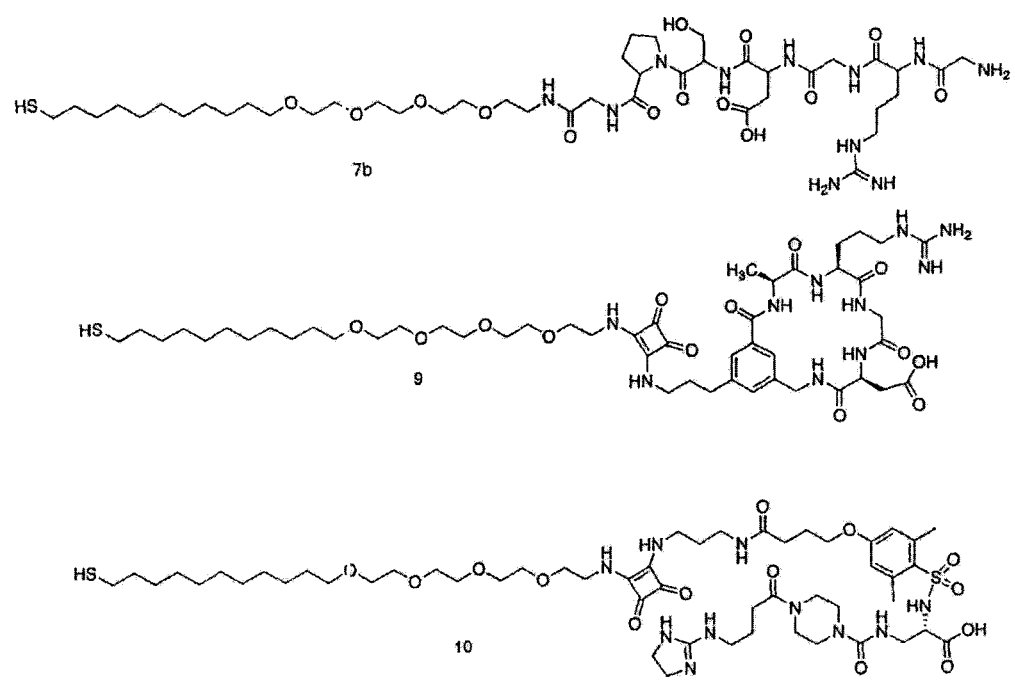
FIGS. 7 and 8 illustrate some of the chemistry for another alternative within the present invention.
Figure 8:
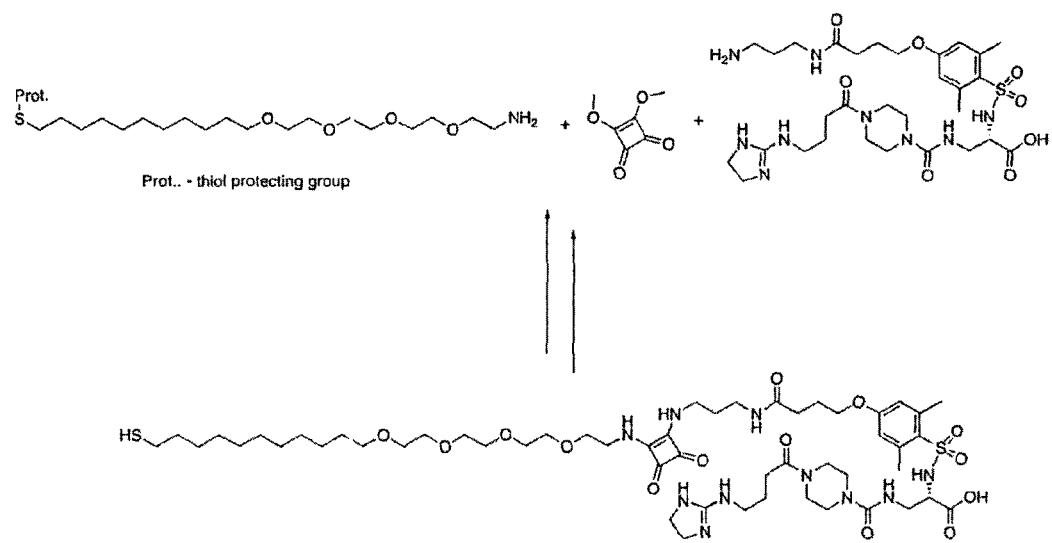

It is also envisioned that the ligand moieties for the SAMs of the present invention can include ligands that are other than peptides. We have tested whether arrays of SAMs can be used to present small organic molecules different from peptides and whether these arrays can be used for functional cell-based screening. We have synthesized three alkane thiols presenting ligands for avb3 integrtins. For integrin ligands, we used a peptide (linear RGD containing peptide), a cyclic inhibitor molecule containing elements of RGD peptide sequence and a known non-peptide integrin inhibitor (FIG. 7). The latter two molecules were synthesized by a straightforward synthetic strategy Eased on coupling of inhibitor molecules presenting amine-linker and protected alkane thiol moiety containing amine linker using squaric acid linkage (FIG. 8). Thus, while peptides may be used to test ligands, the ultimate ligands which might be used to host cells can be non-peptide ligands that provide similar signals to the cells on the array.

Methods and Materials for SAM Synthesis and Assembly

Materials: All reagents for solution phase chemical synthesis were purchased from Aldrich (Milwaukee, Wis.) and used without further purification with the following exception: 2,2'-azobisisobutyronitile (AIBN) was recrystallized from acetone prior to use. Amino acids were protected with 9-fluorenylmethyloxycarbonyl (Fmoc) and 4-(2',4'-Dimethoxyphenyl-Fmoc-aminomethyl)-phenoxy (Rink amide AM) resin was used for the solid phase peptide synthesis (SPPS) and were purchased from NovaBiochem (San Diego, Calif.). N-Hydroxybenzotriazole (HOBt) was purchased from Advanced ChemTech (Louisville, Ky.). Anhydrous tetrahydrofurane (THF) was distilled from Na-benzophenone ketyl. N,N-dimethylformamide (DMF) was vacuum distilled from 4 Å molecular sieves. UV-irradiation at 254 nm was done in a Rayonet Photochemical Chamber Reactor, Model RPR-200. Flash chromatography was performed with silica gel 60, 230-450 mesh (Sorbent Technologies). Preparative HPLC was performed on a Spectra system P2000 instrument with a UV2000 detector. Preparative HPLC conditions used: Vydac® 150 cm×22 mm C-18 reverse-phase column flowing at 10 mL/min using 0.1% TFA as mobile phase A and 0.1% TFA in acetonitrile as mobile phase B. Electrospray ionization (ESI) high resolution mass spectra (HRMS) were obtained with a Micromass LCT™. H-NMR and C-NMR were recorded on a Bruker AC-300. The liquid chromatograph/mass spectrograph (LCMS) used was a Shimadzu LCMS-2010 instrument with photodiode array detector (SPD-M10Avp), and a single quadrupole analyzer. HPLC conditions used for LCMS were: Supelco (Bellefonte, Pa.) 15 cm×2.1 mm C-18 wide-pore reverse-phase column flowing at 200 μL/min using 0.4% formic acid as mobile phase A and 0.2% formic acid in acetonitrile as mobile phase B. All tissue culture reagents were obtained from Gibco/Invitrogen (Carlsbad, Calif.). The cell lines SH-SY5Y and Swiss-3T3 were obtained from American Type Culture Collection (ATCC, Manassas, Va.) and were passage 20 or lower. Vector Red Alkaline Phosphatase Substrate Kit I was obtained from Vector Labs (Burlingame, Calif.). Glass coverslips (Corning No 1½, 23 mm squares) for the array production were purchased from Fisher.

Figure 5:
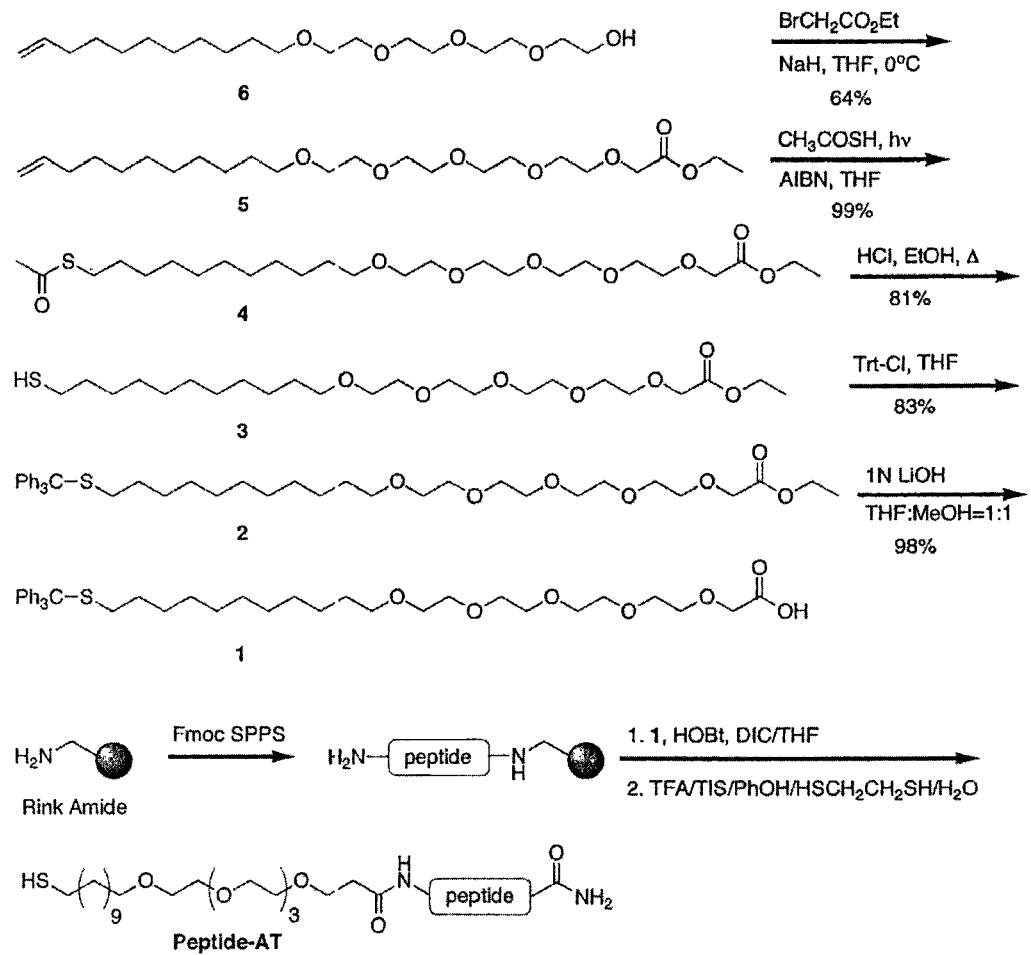
FIG. 5 illustrates one of the synthesis schemes in the material and methods presented below.

Scheme 1: The molecules are illustrated in FIG. 5, and this scheme involves the synthesis of the AT peptide conjugates. The general strategy employed was adapted from Houseman et al. with some modifications in the synthetic steps. In addition the tetra(ethylene glycol) derivative was employed rather than hexa(ethylene glycol). Abbreviations used: TFA, trifluoroacetic acid; TIS, triisopropylsilane; EDT, ethanedithiol; PhOH, phenol.

(2-{2-[2-Undec-10-enyloxy-ethoxy)-ethoxy]-ethoxy}-ethoxy)-acetic acid ethyl ester (5): To a solution of compound $6^2$ (3.00 g, 8.65 mmol) and vacuum-dried KI (331 mg, 1.73 mmol) in dry THF (40 mL) was added sodium hydride (95%, 437 mg, 17.3 mmol). The solution was stirred at room temperature for 3 min under nitrogen and then cooled to 0° C. Ethyl bromoacetate (2.02 mL, 17.2 mmol) was rapidly added and the reaction mixture was stirred for 3 hours at 0° C. The reaction was quenched with 5% aqueous citric acid solution and immediately extracted with dichloromethane (3×50 mL). The combined organic layers were washed with brine, dried over MgSO$_4$ and concentrated with a rotatory evaporator under reduced pressure. Flash chromatography on silica gel (2:1→1:1 hexane/ethyl acetate→ethyl acetate) yielded 5 as a clear oil (2.39 g, 5.52 mmol, 63.8%). H NMR (300 MHz, CDCl$_3$): δ 1.23-1.41 (m, 15H), 1.57 (pent, 2H, J=7 Hz), 1.99-2.08 (m, 2H), 3.45 (t, 2H, J=7 Hz), 3.55-3.76 (m, 18H), 4.15 (s, 2H), 4.22 (q, 2H, J=7 Hz), 4.90-5.04 (m, 2H), 5.82 (ddt, 1H, J=17 Hz, J=10.2 Hz, J=6.5 Hz). C NMR (300 MHz, CDCl$_3$): δ 14.02, 25.88, 28.76, 28.93, 29.24, 29.27, 29.34, 29.42, 33.61, 60.61, 68.54, 69.48, 70.40, 70,69, 71.35, 113.90, 139.03, 170.28. HRMS (ESI) calculated for C$_{23}$H$_{44}$O$_7$Na (M+Na$^+$) m/e 455.2985, found 455.2985.

[2-(2-{2-[2-(11-Acetylsulfanyl-undecyloxy)-ethoxy]-ethoxy}-ethoxy)-ethoxy]-acetic acid ethyl ester (4): A solution of 5 (2.37 g, 5.48 mmol), thioacetic acid (2 mL, 28.5 mmol) and AIBN (15.0 mg, 0.09 mmol) in dry THF (30 mL) was purged with nitrogen for 15 minutes and the solution was irradiated at 254 nm for 10 hours. The reaction mixture was concentrated with a rotatory evapomtor under reduced pressure and purified by silica gel flash-chromatography (eluent 2:1→1:1 hexane/ethyl acetate→ethyl acetate) to yield 4 as a colorless oil (2.76 g, 5.44 mmol, 99.3%). H NMR (300 MHz, CDCl$_3$): δ 1.23-1.40 (m, 19H), 1.50-1.62 (m, 4H), 2.32 (s, 3H), 2.86 (t, 2H, J=7.5 Hz), 3.44 (t, 2H, J=7 Hz), 3.55-3.76 (m, 18H), 4.15 (s, 2H), 4.22 (q, 2H, J=7.5 Hz). C NMR (300 MHz, CDCl$_3$): δ 14.02, 25.88, 28.61, 28.91, 28.95, 29.30, 29.35, 29.43, 30.44, 60.59, 68.53, 69.85, 70.41, 70.68, 71.33, 170.27, 195.85. HRMS (ESI) calculated for C$_{25}$H$_{48}$O$_8$SNa (M+Na$^+$) m/e 531.2963, found 531.2982.

([2-(2-{2-[2-(11-Mercapto-undecyloxy)-ethoxy]-ethoxy}-ethoxy)-ethyxy]-acetic acid ethyl ester (3): A solution of 4 (2.37 g, 4.66 mmol) in absolute ethanol (40 mL) was purged with nitrogen for 15 minutes. An aqueous solution of concentrated HCl (94.0 mL) was added and the resulting mixture was purged with nitrogen for another 5 minutes. The reaction mixture was heated at reflux under nitrogen for 12 hours. The reaction mixture was cooled to room temperature and quenched with 1 M NaOH until the pH of the solution was slightly acidic. The solution was partially concentrated, diluted with water/brine (1:1) (30 mL) and extracted with dichloromethane (3×50 mL). The combined organic layers were concentrated with a rotatory evaporator under reduced pressure and purified by silica gel flash-chromatography (eluent 2:1→1:1 hexane/ethyl acetate→ethyl acetate) to yield 3 as a colorless oil (1.77 g, 3.79 mmol, 81.4%). H NMR (300 MHz, CDCl$_3$): 1.22-1.42 (m, 19H), 1.51-1.66 (m, 4H), 2.52 (q, 2H, J=7.5 Hz), 3.44 (t, 2H, J=7.0 Hz), 3.55-3.76 (m, 18H), 4.15 (s, 2H), 4.21 (q, 2H, J=1.7 Hz). C NMR (300 MHz, CDCl$_3$): δ 14.05, 24.45, 25.87, 28.17, 28.86, 29.29, 29.35, 29.43, 33.85, 60.59, 68.52, 69.84, 70.40, 70.68, 71.33, 170.24. HRMS (ESI) calculated for C$_{23}$H$_{46}$O$_7$SNa (M+Na$^+$) m/e 489.2862, found 489.2844.

([2-(2-{2-[2-(11-Tritylsulfanyl-undecyloxy)-ethoxy]-ethoxy}-ethoxy)-ethoxy]-acetic acid ethyl ester (2): To a solution of 3 (1.75 g, 3.75 mmol) in dry THF (10 mL) was added trityl chloride (2.09 g, 7.50 mmol). The reaction mixture was stirred at room temperature until complete disappearance of 3 as determined by NMR (quartet at 2.5 ppm). The reaction mixture was concentrated with a rotatory evaporator under reduced pressure and purified by silica gel flash-chromatography (eluent: 2:1→1:1→1:2 hexane/ethyl acetate) to yield 2 as a clear oil (2.21 g, 3.11 mmol, 83.2%). H NMR (300 MHz, CDCl$_3$): δ 1.08-1.44 (m, 19H), 1.56 (pent, 2H, J=7 Hz), 2.12 (t, 2H, J=7.3 Hz), 3.44 (t, 2H, J=7 Hz), 3.55-3.72 (m 16H), 4.14 (s, 2H), 4.21 (q, 2H, J=7.1 Hz), 7.16-7.31 (m, 9H), 7.38-7.44 (m, 6H). C NMR (300 MHz, CDCl$_3$): δ 14.44, 26.30, 28.80, 29.23, 29.40, 29.62, 2.9.71, 29.77, 29.85, 32.24, 61.02, 68.94, 70.26, 70.82, 71.10, 71.76, 76.82, 77.24, 77.67, 126.69, 128.00, 129.80, 145.28. HRMS (ESI) calculated for C$_{42}$H$_{60}$O$_7$SNa (M+Na$^+$) m/e 731.3957, found 731.3936.

([2-(2-{2-[2-(11-Tritylsulfanyl-undecyloxy)-ethoxy]-ethoxy}-ethoxy)-ethoxy]-acetic acid) (1): To a solution of 2 (1.63 g, 2.30 mmol) in 1:1 THF/MeOH (50 mL) was added water (2 mL) and solid lithium hydroxide (193 mg, 4.60 mmol). The solution was purged with nitrogen for 10 minutes and stirred at room temperature for 12 hours. The solution was acidified to pH 1 with 1 N HCl, diluted with water/brine (1:1) (20 mL) and immediately extracted with dichloromethane (4×50 mL). The combined organic layers were washed with brine (20 mL), dried over MgSO$_4$ and concentrated to afford 1 as a clear oil (1.526 g, 2.24 mmol, 97.6%). H NMR (300 MHz, CDCl$_3$): δ 1.16-1.45 (m, 16H), 1.57 (pent, 2H, J=7 Hz), 2.13 (t, 2H, J=7.2 Hz), 3.45 (t, 2H, J=6.8 Hz), 3.57-3.78 (m, 14H), 4.16 (s, 2H), 7.17-7.31 (m, 9H), 7.39-7.44 (m, 6H). C NMR (300 MHz, CDCl$_3$): δ 26.25, 28.79, 29.22, 29.40, 29.61, 29.70, 29.74, 32.23, 69.34, 70.10, 70.50, 70.58, 70.61, 70.74, 70.85, 71.56, 71.76, 126.67, 127.98, 129.80, 145.27. HRMS (ESI) calculated for C$_{40}$H$_{56}$O$_7$SNa (M+Na$^+$) m/e 703.364, found 703.3653.

Peptide-ATs. Peptides were synthesized on a Pioneer™ Peptide Synthesis System using standard Fmoc chemistry on Rink Amide AM resin (loading: 0.56 mmol/g). Peptide-alkanethiol conjugates were prepared similarly to the procedure of Houseman et al. Briefly, resin containing protected peptide with a free N-terminus was swollen in dry THF, 5-fold excess of each of the compound 1, HOBt and 1,3-diisopropylcarbodiimide (DIC) was added to the resin suspension in THF. The resin was incubated for 12 hours and another 3-fold excess of DIC and HOBt was added. After 3 hours, the resin was tested with Kaiser test, washed with DMF and dichloromethane and dried in vacuo. After cleavage with TFA/DIC/EDT/H$_2$O/phenol (36:1:1:1:1) for 2 hours and ether precipitation, conjugates were purified by preparative HPLC. Gradient used (percentage of mobile phase A): 100→0% 20 min, 0% 3 min. 0→100% 3 minutes. Peaks at retention time around 17 minutes were collected. Each purified sample was analyzed by LCMS and H NMR. Note: The presence of triplet of 1,1,1-triples δ 2.49 (t[111t], 2H, J=7.1 Hz, J$_{HD}$=1.0 Hz) in H NMR at AT-peptides in CD$_3$OD is indicative of free thiol functionality. It is the signal of methylene hydrogens next to the free thiol functionality (7 NZ, coupling to neighboring methylene, 1 Hz coupling to deuterium on free thiol).

Peptide-AT (GRGDS): $^1$H NMR (300 MHz, CD$_3$OD): δ 1.27-1.45 (m, 15H), 1.51-2.00 (m, 11H), 2.49 (t[111t], 2H, J=7.11, 1.0 Hz, —CH$_2$CH$_2$SD), 2.86 (ABX-quartet, A=2.93 ppm, B=2.80 ppm, J$_{AB}$=17 Hz, J$_{BX}$=7.6 Hz, J$_{AX}$=7.6 Hz), 3.21 (t, 2H, J=6.8 Hz), 3.47 (t, 2H, J=6.7 Hz), 3.55-3.76 (m, 18H), 3.8-3.94 (m, 4H), 3.98 (s, 2H), 4.07 (s, 2H), 4.34-4.41 (m, 2H), 4.74 (t, 1H, J=6.7 Hz). HRMS (ESI) calculated for C$_{38}$H$_{71}$N$_9$O$_{14}$SNa (M+Na$^+$) m/e 932.4739 measured 932.4740.

Peptide-AT (GKGDS): $^1$H NMR (300 MHz, CD$_3$OD): δ 1.25-1.43 (m, 15H), 1.43-1.98 (m, 11H), 2.49 (t[111t], 2H, J=7 Hz, J$_{HD}$=1.0 Hz, —CH$_2$CH$_2$SD), 2.73-2.83 (m, 1H), 2.89-2.99 (m, 3H), 3.47 (t, 2H, J=6.7 Hz), 3.55-3.76 (m, 18H), 3.8-3.94 (m, 4H), 3.96 (s, 2H), 4.08 (s, 2H), 4.34-4.41 (m, 2H), 4.73 (t, 1H, J=67 Hz). MS (LCMS) calculated for C$_{38}$H$_{72}$N$_7$O$_{14}$S (M+H$^+$) m/e 882.48 measured 882.30.

Peptide-AT (GSDPGYIGSR): $^1$H NMR (300 MHz, CD$_3$OD): δ 0.87-0.97 (m, 7H) 1.27-1.47 (m, 21H), 1.48-2.13 9m, 17H), 2.49 (t[111t], 2H, J=7.1 Hz, J$_{HD}$-1.0 Hz, —CH$_2$CH$_2$SD), 2.65-2.77 (m, 1H), 2.94-3.24 (m, 6H, 3.46 (t, 2H, J=6.7 Hz), 3.54-3.74 (m, 18H), 3.74-4.08 (m, 15H), 4.31-4.52 (m, 5H) 4.98-5.07 (m, 1H), 6.7 (d, 2H, J=8.6 Hz), 7.06 (d, 2H, J=8.6 Hz), 7.91-8.46 (m, 3H). MS (LCMS) calculated for C$_{63}$H$_{108}$N$_{14}$O$_{21}$S (M+2H+) m/e 714.35, found 714.40.

Figure 6:
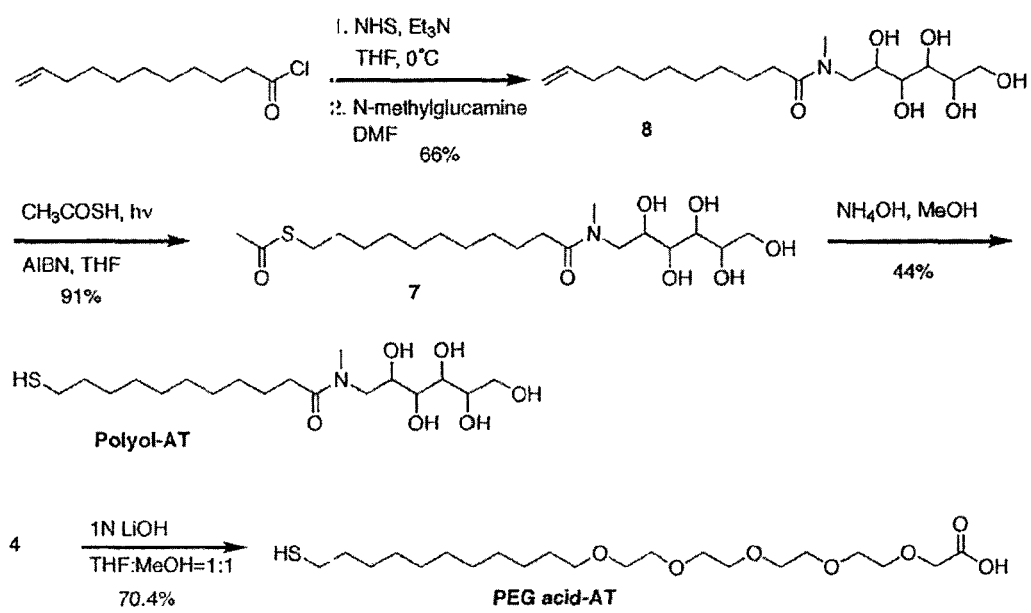
FIG. 6 illustrates another step in the synthesis scheme presented in the methods and materials below.

Scheme 2: Synthesis; of the polyol-AT and PEG acid-AT is illustrated in FIG. 6.

(Undec-10-enoic acid methyl-(2,3,4,5,6-pentahydroxy-hexyl)-amide) (8) To a solution of N-hydroxy succinimide (NHS) in dry THF (30 mL) triethylamine (1.03 mL, 7.38 mmol) was added and the reaction mixture was cooled to 0° C. Undecenoyl chloride (944 µL, 4.93 mmol) was added dropwise. The reaction mixture was warmed slowly to room temperature and stirred for 1 hour. The reaction was quenched with 5% citric acid (100 mL), dichloromethane (100 mL) was added, the organic layer was separated, washed with brine, dried over MgSO$_4$ and concentrated to afford undecenoyl-HNS-ester that was used without further purification. The undecenoyl-NHS-ester was dissolved in amine-free DMF (20 mL) and N-methyl glucamine (0.963 g, 4.93 mmol) was added. The reaction mixture was stirred vigorously at room temperature for four hours. (N-methyl glucamine dissolves slowly during the reaction). DMF was removed with a rotatory evaporator under reduced pressure to dryness and further eliminated in vacuo and the reaction mixture was purified by silica gel chromatography (eluent 5%→7%→10% methanol in dichloromethane) to yield 8 as a white solid (1.17 g, 3.23 mmol, 65.7%). H NMR (300 MHz, CD$_3$OD): δ 1.28-1.43 (m, 10H), 1.54-1.67 (q, 2H, J=7 Hz), 2.39 (t, 1.1H, J=7.6 Hz), 2.48 (t, 0.9H, J=7.6 Hz), 2.86 (t, 2H, J=7.5 Hz), 2.96 (s, 1.4H), 3.14 (s, 1.6H), 3.34-3.46 (m, 1H), 3.56-3.81 (m, 6H), 3.94-4.00 (m, 1H), 4.88-5.02 (m, 2H), 5.80 (ddt, 1H, J=17 Hz, J=10.2 Hz, J=6.6 Hz). C NMR (300 MHz, CD$_3$OD): δ 26.35, 26.43, 26.78, 30.26, 30.34, 30.61, 30.67. 34.21, 34.59, 34.72, 35.04, 38.13, 52.69, 54.03, 64.88, 71.28, 71.70, 71.41, 73.04, 73.11, 73.20, 73.73, 74.26, 114.85, 140.27, 176.76. Note: all NMR spectra of the polyol-AT and its precursors are complicated by slow rotation around the secondary amide bond. The signals of nuclei close to the amide bond are split into two signals in roughly a 0.88 to 1.0 ratio. For example signals 2.96 (s, 1.4H) and 3.14 (s, 1.6H) corresponding to the N-methyl group in the cis- and trans-amide bond conformations. HRMS (ESI) calculated for C$_{18}$H$_{35}$O$_6$NNa (M+Na$^+$) m/e 384.2362, found 384.2372.

Thioacetic acid S-{10-[methyl-(2,3,4,5,6-pentahydroxy-hexyl)-carbamoyl]-decyl}ester (7): A solution of compound 8 (1.14 g, 3.15 mmol), thioacetic acid (1.00 mL, 14.3 mmol) and AIBN (15.0 mg, 0.090 mmol) in dry THF (100 mL) as purged with nitrogen for 15 minutes and reaction mixture was irradiated at 254 nm for 10 hours. Solvent was removed with a rotatory evaporator under reduced pressure and the reaction mixture was purified by silica gel chromatography (eluent 5%→7%→10%→15% methanol in dichloromethane) to yield 7 as a white solid (1.25 g, 2.85 mmol, 90.6%). H NMR (300 MHz, CD$_3$OD): δ 1.27-1.40 (m, 12H), 1.50-1.65 (m, 4H), 2.30 (s, 3H), 2.39 (t, 1.1H, J=7.6 Hz), 2.48 (t, 0.9H, J=7.6 Hz), 2.86 (t, 2H, J=7.5 Hz), 2.96 (s, 1.4H), 3.14 (s, 1.6H), 3.34-3.46 (m, 1H), 3.56-3.81 (m, 6H), 3.94-4.00 (m, 1H). C NMR (300 MHz, CD$_3$OD): δ 26.33, 26.76, 29.91, 29.97, 30.32, 30.59, 30.67, 30.88, 34.20, 34.58, 34.73, 38.08, 52.63, 54.02, 64.79, 71.15, 71.60, 72.38, 72.93, 73.05, 73.15, 73.70, 74.18, 176.73, 176.78, 197.69. HRMS (ESI) calculated for C$_{20}$H$_{39}$NO$_7$SNa (M+Na$^+$) m/e 460.2345, found 460.2354.

11-Mercapto-undecanoic acid methyl-(2,3,4,5,6-pentahydroxy-hexyl)-amide (polyol-AT): A solution of 7 (200 mg, 0.457 mmol) in methanol (2.00 mL) was purged with nitrogen for 10 minutes. Ammonia (2 M in methanol, 456 µL) was added and the reaction mixture was stirred for 12 hours under nitrogen. The reaction was quenched using Amberlyst IR-1200 acidic resin. The resin was added until the pH was neutral. The resin was filtered, the solvent was removed with a rotatory evaporator under reduced pressure and reaction mixture was purified by silica gel chromatography (eluent 5%→7%→10%→15% methanol in dichloromethane) to yield Polyol-AT as a white solid (80.0 mg, 0.202 mmol, 44%). H NMR (300 MHz, CD$_3$OD): δ 1.27-1.44 (m, 12H), 1.54-1.66 (m, 4H), 2.39 (t, 1H, J=7.6 Hz), 2.44-2.52 (m, 3H) {most likely 2 overlapped signals: 2.48 (t, 1H, J=7.6 Hz, —CH$_2$CH$_2$C(O)N) and 2.49 (t[111t], J=Hz, J$_{HD}$=1 Hz, —CH$_2$CH$_2$SD)}, 2.96 (s, 1.4H), 3.14 (s, 1.6H), 3.34-3.46 (m, 1H), 3.56-3.81 (m, 6H), 3.93-4.01 (m, 1H). C NMR (300 MHz, CD$_3$OD): δ 25.11, 26.35, 26.77, 29.56, 30.35, 30.62, 30.72, 30.765, 34.22, 34.60, 34.72. 35.38, 38.13, 52.68, 54.03, 64.87, 71.26, 71.69, 72.41, 73.03, 73.10, 73.19, 73.73, 74.26, 176.77, 176.85. HRMS (ESI) calculated for C$_{18}$H$_{36}$NO$_6$S ([M-H]$^-$) m/e 394.2263, found 394.2281.

[2-(2-{2-(11-Mercapto-undecyloxy)-ethoxy]-ethoxy}-ethoxy)-ethoxy}-acetic acid (PEG acid-AT): A solution of compound 4 (100 mg, 0.196 mmol) in methanol/THF (1:1) (4 mL) was purged with nitrogen for 10 minutes. Aqueous LiOH (1 M) was purged with N$_2$ for 5 minutes and then added (486 µL) to the THF solution. The resulting solution was purged for 5 minutes and stirred under nitrogen for 12 hours. To the reaction was added 1 N HCl until the pH was 1. A solution of brine-water (1:1) was added (10 mL) and the mixture was extracted with dichloromethane (5×20 mL). Flash chromatography on silica gel (eluent 5%→10% methanol in dichloromethane with 0.5% acetic acid) yielded PEG acid-AT as colorless, viscous oil (60.5 mg, 0.138 mmol, 70.4%). H NMR (300 MHz, CDCl$_3$): δ 1.22-1.40 (m, 15H), 1.51-1.65 (m, 4H), 2.52 (q, 2H, J=7.5 Hz), 3.45 (t, 2H, J=7 Hz), 3.55-3.77 (m, 16H), 4.15 (s, 2H), 8.2-9.1 (br s, 1H). C NMR (300 MHz, CDCl$_3$): δ 24.82, 26.21, 28.53, 28.69, 29.14, 29.23, 29.40, 29.68, 34.21, 69.19, 70.06, 70.47, 70.56, 70.66, 70.74, 71.40, 71.70, 172.82. HRMS (ESI) calculated for C$_{21}$H$_{41}$O$_7$S ([M-H]$^-$) m/e 437.2573, found 437.2552.

(12,12,13,13,14,14,15,15,16,16,17,17,18,18,19,19,19-Heptadecafluoro-nonadecane-1-thiol)(Fluoro-AT): This synthesis was performed according to the procedure of Graupe et al. with the exception that LiAlH$_4$ was used to reduce the alkyl-iodide and thioester moiety instead of the published NaBH$_4$.

The invention claimed is:

1. A human stem cell culture comprising:
human stem cells, a medium in which human stem cells will grow, and a self-assembled monolayer presenting to the human stem cells molecules of a peptide ligand that supports the growth of human stem cells in an undifferentiated state, wherein the peptide ligand consists essentially of a receptor recognition epitope, wherein the monolayer comprises a plurality of elements, each element comprising an attachment moiety, an alkane spacer moiety attached to the attachment moiety, and a peptide ligand covalently attached to the spacer moiety such that all peptide ligands within an array element are presented on the array in a uniform orientation, the monolayer arranged on an inert substrate with the attachment moiety of each element attached to the substrate.

2. A human stem cell culture as claimed in claim 1, wherein the peptide ligand is selected from the group consisting of SDPGYIGSR (SEQ ID NO:2), GRNIAEIIKDI (SEQ ID NO:3), DITYVRLKF (SEQ ID NO:4), DITVTLNRL (SEQ ID NO:5), GRYVVLPR (SEQ ID NO:6), GNRWHSIYITRFG (SEQ ID NO:7), SIDQVEPYSSTAQ (SEQ ID NO:8), KIPKASSVPTELSAISTLYL (SEQ ID NO:9), KKQRFRHRNRKG (SEQ ID NO:10), GASIKVAVSADR (SEQ ID NO:11), GTTVKYIFR (SEQ ID NO:12), GSIKIRGTYS (SEQ ID NO:13) and GSINNNR (SEQ ID NO:14).

3. A self-assembled monolayer presenting molecules of a peptide ligand that support the growth of human stem cells in an undifferentiated state, wherein the peptide ligand consists essentially of a receptor recognition epitope, wherein the monolayer comprises a plurality of elements, each element comprising an attachment moiety, an alkane spacer moiety attached to the attachment moiety, and a peptide ligand covalently attached to the spacer moiety such that all peptide ligands within an array element are presented on the array in a uniform orientation, the monolayer arranged on an inert substrate with the attachment moiety of each element attached to the substrate.

4. A self-assembled monolayer as claimed in claim 3, wherein the peptide ligand is selected from the group consisting of SDPGYIGSR (SEQ ID NO:2), GRNIAEIIKDI (SEQ ID NO:3), DITYVRLKF (SEQ ID NO:4), DITVTLNRL (SEQ ID NO:5), GRYVVLPR (SEQ ID NO:6), GNRWHSIYITRFG (SEQ ID NO:7), SIDQVEPYSSTAQ (SEQ ID NO:8), KIPKASSVPTELSAISTLYL (SEQ ID NO:9), KKQRFRHRNRKG (SEQ ID NO:10), GASIKVAVSADR (SEQ ID NO:11), GTTVKYIFR (SEQ ID NO:12), GSIKIRGTYS (SEQ ID NO:13) and GSINNNR (SEQ ID NO:14).

5. A method for culturing undifferentiated human stem cells, the method comprising the steps of:
applying the stem cells and a medium in which human stem cells will grow to a self-assembled monolayer presenting to the human stem cells molecules of a peptide ligand that support the growth of human stem cells in an undifferentiated state, wherein the monolayer comprises a plurality of elements, each element comprising an attachment moiety, an alkane spacer moiety attached to the attachment moiety, and a peptide ligand covalently attached to the spacer moiety such that all peptide ligands within an array element are presented on the array in a uniform orientation, the monolayer arranged on an inert substrate with the attachment moiety of each element attached to the substrate, wherein the peptide ligand consists essentially of a receptor recognition epitope; and
culturing the cells under conditions that favor the growth of cells.

6. A method as claimed in claim 5, wherein the peptide ligand is selected from the group consisting of SDPGYIGSR (SEQ ID NO:2), GRNIAEIIKDI (SEQ ID NO:3), DITYVRLKF (SEQ ID NO:4), DITVTLNRL (SEQ ID NO:5), GRYVLPR (SEQ ID NO:6), GNRWHSIYITRFG (SEQ ID NO:7), SIDQVEPYSSTAQ (SEQ ID NO:8), KIPKASSVPTELSAISTLYL (SEQ ID NO:9), KKQRFRHRNRKG (SEQ ID NO:10), GASIKVAVSADR (SEQ ID NO:11), GTTVKYIFR (SEQ ID NO:12), GSIKIRGTYS (SEQ ID NO:13) and GSINNNR (SEQ ID NO:14).

* * * * *

SEQUENCE LISTING

<160> NUMBER OF SEQ ID NOS: 27

<210> SEQ ID NO 1
<211> LENGTH: 5
<212> TYPE: PRT
<213> ORGANISM: Artificial
<220> FEATURE:

<223> OTHER INFORMATION: Synthetic peptide

<400> SEQUENCE: 1

Tyr Ile Gly Ser Arg
1               5

<210> SEQ ID NO 2
<211> LENGTH: 9
<212> TYPE: PRT
<213> ORGANISM: Artificial
<220> FEATURE:
<223> OTHER INFORMATION: Synthetic peptide

<400> SEQUENCE: 2

Ser Asp Pro Gly Tyr Ile Gly Ser Arg
1               5

<210> SEQ ID NO 3
<211> LENGTH: 11
<212> TYPE: PRT
<213> ORGANISM: Artificial
<220> FEATURE:
<223> OTHER INFORMATION: Synthetic peptide

<400> SEQUENCE: 3

Gly Arg Asn Ile Ala Glu Ile Ile Lys Asp Ile
1               5                   10

<210> SEQ ID NO 4
<211> LENGTH: 9
<212> TYPE: PRT
<213> ORGANISM: Artificial
<220> FEATURE:
<223> OTHER INFORMATION: Synthetic peptide

<400> SEQUENCE: 4

Asp Ile Thr Tyr Val Arg Leu Lys Phe
1               5

<210> SEQ ID NO 5
<211> LENGTH: 9
<212> TYPE: PRT
<213> ORGANISM: Artificial
<220> FEATURE:
<223> OTHER INFORMATION: Synthetic peptide

<400> SEQUENCE: 5

Asp Ile Arg Val Thr Leu Asn Arg Leu
1               5

<210> SEQ ID NO 6
<211> LENGTH: 8
<212> TYPE: PRT
<213> ORGANISM: Artificial
<220> FEATURE:
<223> OTHER INFORMATION: Synthetic peptide

<400> SEQUENCE: 6

Gly Arg Tyr Val Val Leu Pro Arg
1               5

<210> SEQ ID NO 7
<211> LENGTH: 13
<212> TYPE: PRT
<213> ORGANISM: Artificial
<220> FEATURE:
<223> OTHER INFORMATION: Synthetic peptide

```
<400> SEQUENCE: 7

Gly Asn Arg Trp His Ser Ile Tyr Ile Thr Arg Phe Gly
1               5                   10

<210> SEQ ID NO 8
<211> LENGTH: 13
<212> TYPE: PRT
<213> ORGANISM: Artificial
<220> FEATURE:
<223> OTHER INFORMATION: Synthetic peptide

<400> SEQUENCE: 8

Ser Ile Asp Gln Val Glu Pro Tyr Ser Ser Thr Ala Gln
1               5                   10

<210> SEQ ID NO 9
<211> LENGTH: 20
<212> TYPE: PRT
<213> ORGANISM: Artificial
<220> FEATURE:
<223> OTHER INFORMATION: Synthetic peptide

<400> SEQUENCE: 9

Lys Ile Pro Lys Ala Ser Ser Val Pro Thr Glu Leu Ser Ala Ile Ser
1               5                   10                  15

Thr Leu Tyr Leu
            20

<210> SEQ ID NO 10
<211> LENGTH: 12
<212> TYPE: PRT
<213> ORGANISM: Artificial
<220> FEATURE:
<223> OTHER INFORMATION: Synthetic peptide

<400> SEQUENCE: 10

Lys Lys Gln Arg Phe Arg His Arg Asn Arg Lys Gly
1               5                   10

<210> SEQ ID NO 11
<211> LENGTH: 12
<212> TYPE: PRT
<213> ORGANISM: Artificial
<220> FEATURE:
<223> OTHER INFORMATION: Synthetic peptide

<400> SEQUENCE: 11

Gly Ala Ser Ile Lys Val Ala Val Ser Ala Asp Arg
1               5                   10

<210> SEQ ID NO 12
<211> LENGTH: 9
<212> TYPE: PRT
<213> ORGANISM: Artificial
<220> FEATURE:
<223> OTHER INFORMATION: Synthetic peptide

<400> SEQUENCE: 12

Gly Thr Thr Val Lys Tyr Ile Phe Arg
1               5

<210> SEQ ID NO 13
<211> LENGTH: 10
<212> TYPE: PRT
<213> ORGANISM: Artificial
<220> FEATURE:
<223> OTHER INFORMATION: Synthetic peptide
```

```
<400> SEQUENCE: 13

Gly Ser Ile Lys Ile Arg Gly Thr Tyr Ser
1               5                   10

<210> SEQ ID NO 14
<211> LENGTH: 7
<212> TYPE: PRT
<213> ORGANISM: Artificial
<220> FEATURE:
<223> OTHER INFORMATION: Synthetic peptide

<400> SEQUENCE: 14

Gly Ser Ile Asn Asn Asn Arg
1               5

<210> SEQ ID NO 15
<211> LENGTH: 7
<212> TYPE: PRT
<213> ORGANISM: Artificial
<220> FEATURE:
<223> OTHER INFORMATION: Synthetic peptide

<400> SEQUENCE: 15

Gly Arg Gly Asp Ser Pro Lys
1               5

<210> SEQ ID NO 16
<211> LENGTH: 7
<212> TYPE: PRT
<213> ORGANISM: Artificial
<220> FEATURE:
<223> OTHER INFORMATION: Synthetic peptide

<400> SEQUENCE: 16

Gly Arg Gly Ser Asp Pro Lys
1               5

<210> SEQ ID NO 17
<211> LENGTH: 13
<212> TYPE: PRT
<213> ORGANISM: Artificial
<220> FEATURE:
<223> OTHER INFORMATION: Synthetic peptide

<400> SEQUENCE: 17

Gly Arg Lys Arg Leu Gln Val Gln Leu Ser Ile Arg Thr
1               5                   10

<210> SEQ ID NO 18
<211> LENGTH: 13
<212> TYPE: PRT
<213> ORGANISM: Artificial
<220> FEATURE:
<223> OTHER INFORMATION: Synthetic peptide

<400> SEQUENCE: 18

Gly Thr Trp Tyr Lys Ile Ala Phe Gln Arg Asn Arg Lys
1               5                   10

<210> SEQ ID NO 19
<211> LENGTH: 9
<212> TYPE: PRT
<213> ORGANISM: Artificial
<220> FEATURE:
<223> OTHER INFORMATION: Synthetic peptide

<400> SEQUENCE: 19
```

Gly Asp Phe Lys Leu Phe Ala Val Tyr
1               5

<210> SEQ ID NO 20
<211> LENGTH: 10
<212> TYPE: PRT
<213> ORGANISM: Artificial
<220> FEATURE:
<223> OTHER INFORMATION: Synthetic peptide

<400> SEQUENCE: 20

Gly Ser Asp Pro Gly Tyr Ile Gly Ser Arg
1               5                   10

<210> SEQ ID NO 21
<211> LENGTH: 6
<212> TYPE: PRT
<213> ORGANISM: Artificial
<220> FEATURE:
<223> OTHER INFORMATION: Synthetic peptide

<400> SEQUENCE: 21

Gly Pro Asp Ser Gly Arg
1               5

<210> SEQ ID NO 22
<211> LENGTH: 13
<212> TYPE: PRT
<213> ORGANISM: Artificial
<220> FEATURE:
<223> OTHER INFORMATION: Synthetic peptide

<400> SEQUENCE: 22

Gly Ser Leu Val Arg Asn Arg Arg Val Ile Thr Ile Gln
1               5                   10

<210> SEQ ID NO 23
<211> LENGTH: 10
<212> TYPE: PRT
<213> ORGANISM: Artificial
<220> FEATURE:
<223> OTHER INFORMATION: Synthetic peptide

<400> SEQUENCE: 23

Gly Asp Ile Thr Tyr Val Arg Leu Lys Phe
1               5                   10

<210> SEQ ID NO 24
<211> LENGTH: 10
<212> TYPE: PRT
<213> ORGANISM: Artificial
<220> FEATURE:
<223> OTHER INFORMATION: Synthetic peptide

<400> SEQUENCE: 24

Gly Asp Ile Arg Val Thr Leu Asn Arg Leu
1               5                   10

<210> SEQ ID NO 25
<211> LENGTH: 11
<212> TYPE: PRT
<213> ORGANISM: Artificial
<220> FEATURE:
<223> OTHER INFORMATION: Synthetic peptide

<400> SEQUENCE: 25

Gly Thr Ser Ile Lys Ile Arg Gly Thr Tyr Ser
1               5                   10

```
<210> SEQ ID NO 26
<211> LENGTH: 7
<212> TYPE: PRT
<213> ORGANISM: Artificial
<220> FEATURE:
<223> OTHER INFORMATION: Synthetic peptide

<400> SEQUENCE: 26

Gly Leu Gly Thr Ile Pro Gly
1               5

<210> SEQ ID NO 27
<211> LENGTH: 11
<212> TYPE: PRT
<213> ORGANISM: Artificial
<220> FEATURE:
<223> OTHER INFORMATION: Synthetic peptide

<400> SEQUENCE: 27

Ile Glu Ile Asn Ala Arg Ile Asp Ile Lys Gly
1               5                   10
```